United States Patent [19]

Smestad et al.

[11] Patent Number: 5,035,715
[45] Date of Patent: Jul. 30, 1991

[54] GAMMA IRRADIATION OF COLLAGEN/MINERAL MIXTURES

[75] Inventors: Thomas L. Smestad, Palo Alto; Daniel Prowse, Los Gatos; George H. Chu, Cupertino; Diana M. Hendricks, Brea, all of Calif.

[73] Assignee: Collagen Corporation, Palo Alto, Calif.

[21] Appl. No.: 356,453

[22] Filed: May 24, 1989

Related U.S. Application Data

[62] Division of Ser. No. 928,306, Nov. 6, 1986, Pat. No. 4,865,602.

[51] Int. Cl.⁵ .............................................. A61F 2/28
[52] U.S. Cl. ................................. 623/16; 128/DIG. 8
[58] Field of Search ..................... 623/16; 128/DIG. 8

[56] References Cited

U.S. PATENT DOCUMENTS 3,443,261  5/1969  Battista et al. .
3,767,437  10/1973 Cruz et al. .
3,949,073  4/1976  Daniels et al. .
4,140,537  2/1979  Luck et al. .
4,291,013  9/1981  Wahlig et al. .
4,424,208  1/1984  Wallace .
4,516,276  5/1985  Mittelmeier et al. .
4,553,974  11/1985 Dewanjee .
4,582,640  4/1986  Smestad .
4,623,553  11/1986 Ries et al. .
4,642,117  2/1987  Nguyen .
4,789,663  12/1988 Wallace et al. .
4,795,467  1/1989  Piez et al. .
4,865,602  9/1989  Smestad et al. .

FOREIGN PATENT DOCUMENTS 0030583  6/1981  European Pat. Off. .......... 623/16 D
 246638  11/1987 European Pat. Off. .
0058041  4/1983  Japan ................................ 623/16 D Primary Examiner—Randall L. Green
Assistant Examiner—Paul Prebilic
Attorney, Agent, or Firm—Irell & Manella

[57] ABSTRACT

A biocompatible collagen/mineral composition which comprises a mixture of 2-40% reconstituted fibrillar atelopeptide collagen and 60-98% calcium phosphate mineral by weight, exclusive of water, is disclosed. The composition has a sterility assurance factor of at least as low as $10^{-6}$ and either a compressive modulus of at least 10 N/cm$^{-2}$ or a tensile strength of about 3-12 N/cm$^{-2}$.

6 Claims, 2 Drawing Sheets

GAMMA IRRADIATION OF COLLAGEN/MINERAL MIXTURES

RELATED APPLICATION

This application is a divisional continuation-in-part of copending U.S. Pat. Application Ser. No. 928,306, filed 6 Nov. 1986, now U.S. Pat. No. 4,865,602.

TECHNICAL FIELD

The invention relates to preparation of implants and prostheses for hard tissue repair composed of collagen and a mineral. In particular, mixtures of atelopeptide fibrillar reconstituted collagen are mixed with a calcium phosphate mineral and the mixtures are treated with gamma irradiation to improve both biological and handling properties.

BACKGROUND ART

A wide range of materials has been proposed for use in repairing hard tissues. For weight-bearing areas, prostheses which are capable of withstanding stress have ranged from metal rods to reconstituted animal bone. Various packing materials have also been used for augmentation of bony structures, such as the use of cross-linked collagen for alveolar ridge augmentation. It is desirable to have available a variety of materials suitable for the various types of skeletal repair, as each application has its unique set of parameters to determine the optimum implant. In addition, the physical handling properties of the material as it is manipulated by the medical practitioner is significant in permitting the practitioner to achieve a successful result, in part because the ease of manipulation determines the ability to succeed.

Attempts have been made to compose suitable materials of the chief organic and inorganic components of bone, namely, collagen and calcium phosphate mineral. Reports of attempts to use the collagen/mineral combination are numerous. For example, J. Lemons et al, reported at the Second World Congress of Biomaterials in Washington, D.C., 27 Apr. 1 May 1984, on attempts to utilize collagen along with commercial hydroxyapatite and calcium phosphate to repair artificially created lesions in rabbits. The use of these mixtures did not result in reunion of the lesions. A control experiment using fresh autogenous bone, however, was successful in producing a union. Similarly, P. Levy et al, *J Periodontal* (1981) 50:303-306, were unsuccessful in their attempts to utilize collagen/mineral gel implants to repair intra-bony defects in root canals of canine or monkey teeth. B.C. Gross et al, *Oral Surg* (1980) 49:21-26, reported limited success in using mixtures of reconstituted lyophilized calfskin collagen in admixture with a hydroxyapatite preparation to induce bone growth through subperiosteal implants in monkeys. Various others have reported use of forms of collagen which clearly contain telopeptides, a major source of immunogenicity of collagen, in combination with minerals in bone repair. See, for example, K. Hayashi et al, *Arch Orthop Traumat Surg* (1982) 99:265-269; Battista, U.S. Pat. No. 4,349,490 (using a hydrated gelatin); Cruz, Jr., U.S. Pat. No. 3,767,437 (using a calcium-precipitated form of collagen); and Battista et al, U.S. Pat. No. 3,443,261 (utilizing, in addition to calcium phosphate, a "new form" of collagen which contains microcrystals of aggregated tropocollagen units.

Miyata et al, U.S. Pat. No. 4,314,380, utilized a mineral backbone prepared directly by treatment of animal bone to remove all organic materials, which was then coated with an atelopeptide collagen. Japanese Application J58/058041, published 6 April 1983, disclosed a spongy porous calcium phosphate material having pores treated with atelopeptide collagen. The collagen derives from collagen-in-solution having a concentration of not more than 2% by weight. The Japanese application reports the advance of osteoblasts into the pores of the material and new bone growth. European Patent Application, Publication No. 030583, published 24 June 1981, disclosed use of collagen fleece in admixture with hydroxyapatite in bone repair. This collagen material is a commercial product, is obtained from animal hide by proteolytic digestion, and is lyophilized and sterilized by gamma irradiation. This collagen preparation forms a soft membrane-like material but does contain telopeptides and is partially degraded by the processing.

EPO application Publication No. 164,483, published 18 Dec. 1985, disclosed a process which is asserted to provide biocompatibility of a mineral/collagen mixture. In this mixture, solubilized collagen is cross-linked either in the presence of, or before the addition of, a calcium phosphate mineral component just to the point wherein it retains its resorbability and absorptive capacity with respect to body fluids, rather than permitting the cross-linking to proceed to completion. U.S. Pat. No. 4,516,276 to Mittelmeier disclosed the combination of a nonfibrillar, nonreconstituted collagen along with hydroxyapatite.

U.S. Pat. application Ser. No. 848,443, filed 4 Apr. 1986, and its parent, U.S. Ser. No. 717,072, filed 28 Mar. 1985, both assigned to the same assignee as the application herein and incorporated by reference, disclose novel compositions containing reconstituted fibrillar atelopeptide collagen in admixture with a calcium phosphate mineral. Various methods are also disclosed for strengthening the composition, which methods include incubation of the mixture at specified temperatures and times, and the treatment of the dried mixture with heat. The preparation of the referenced applications, in order to be non-infective to treated subjects, must be prepared under aseptic conditions, as there is no provision in the disclosed procedures for direct sterilization. Typically, aseptic processing results in products with sterility assurance levels (i.e., probability of a non-sterile product unit) between $10^{-3}$ and $10^{-4}$.

The material which results after the various curing treatments disclosed in the above-referenced applications has a compressibility above 6 Newtons per square centimeter ($N/cm^2$). Both this strength and further improvement in the compressibility indices are achievable by the curing processes disclosed therein.

The art offers no suitable composition for bone defect repair which is readily and efficiently sterilizable while retaining the efficient handling properties desired to permit effective insertion of the implant. The material should be resistant to compression, and yet sufficiently resilient to permit shaping into place, or, alternatively, if to be used in a weight-bearing area, should be suitably rigid. The process and resulting product of the present invention remedies this omission in the art.

The invention takes advantage of an irradiation process which has previously been disclosed with regard to its impact on physical properties only in regard to preparations containing collagen alone. A summary of the effect of gamma-ray irradiation on collagen sutures, for example, is found in Artandi, Technical Report #149, Intl Atomic Energy Agency, Vienna, *Manual on Radiation Sterilization of Medical & Biological Materials* (1973) chap. 15, and a review of the effect of radiation on collagen as a tissue component is published by A.J. Bailey, *Internat Rev Connect Tis* (1968) pp. 233–281. In addition, PCT application WO81/00963 disclosed that collagen materials can be increased in physical strength by heat treatment and by subjecting them to treatment with gaseous hydrogen halide. However, Applicant is aware of no disclosure in the art which shows the effect of gamma-ray irradiation on the physical properties and handling properties of collagen/ mineral mixtures, although gamma-ray irradiation has been used to sterilize the lyophilized preparations disclosed in EPO publication No. 164,483 (supra) without further comment concerning either properties or further use.

DISCLOSURE OF THE INVENTION

The invention provides a process whereby collagen/mineral preparations can be efficiently sterilized and simultaneously have conferred upon them properties which are especially favorable for handling of the material in defect repair, and for their behavior as implants. The heart of the process is irradiation of the preparation with sufficient total energy to effect sterilization to the required level, wherein the collagen/mineral preparation is furnished in such form that the irradiation also provides a satisfactory compressibility modulus as well as the resilience and rigidity combination desired. A range of desired properties is available, depending on the adjustment of the condition or status with regard to relevant parameters of the collagen/mineral sample during the irradiation period.

Accordingly, in one aspect, the invention relates to a method for conferring desired physical properties and sterility levels on a collagen/mineral mixture, which process comprises irradiating the mixture with a sterilizing amount of gamma radiation, typically between 0.5 and 4 Mrad, wherein the mixture comprises about 60–98% of a calcium phosphate mineral and 2–40% of an atelopeptide fibrillar reconstituted collagen exclusive of moisture. During the irradiation, it is important that the collagen portion of the preparation undergo or have undergone sufficient cross-linking to stabilize the physical properties. This can be achieved in a variety of ways, for example, by preheating the sample to effect partial cross-linking or by adjusting the humidity under which irradiation occurs so that the radiation itself effects the desired level of cross-linking. Thus, under these conditions, not only does sterilization to a sterility assurance level of at least as low as $10^{-6}$ take place, but also adjustment of the physical properties occurs by achieving a balance between cross-linking and degradation due to the radiation.

BRIEF DESCRIPTION OF THE DRAWINGS

FIGS. 2a, 2b, 3a, and 3b are discussed in Example 2.

MODES OF CARRYING OUT THE INVENTION

Figure 1:
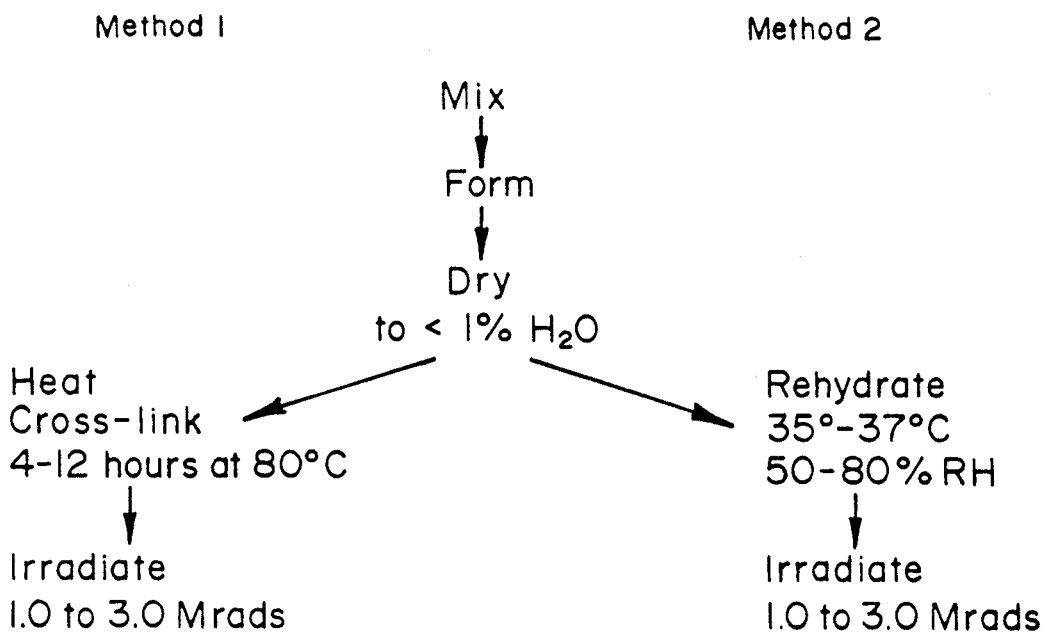
FIG. 1 shows a diagram of alternative methods for carrying out the invention.

The method of the invention is applicable to collagen/mineral mixtures of defined composition. There follows first a discussion of the nature of the individual components and the manner in which they are formed into mixtures.

The Mineral Component

The compositions of the invention can use a variety of calcium phosphate mineral component materials. As used herein, "calcium phosphate mineral" materials refers to those materials composed of $Ca^{+2}$ and phosphate ions, regardless of the microstructure, protonation status of the phosphate, or extent of hydration. Calcium phosphate mineral materials include a variety of forms, such as the commercially available forms of tricalcium phosphate, for example, Synthograft ® tricalcium phosphate, or of hydroxyapatite such as Periograf ®, Alveograf ®, Interpore ®, OrthoMatrix ™ HA1000 ™, or OrthoMatrix ™ HA-500 ™ hydroxyapatite particulate preparations. The presently preferred calcium phosphate mineral is a porous calcium phosphate ceramic granules (0.5–1 mm) (a 60%/40% hydroxyapatite/beta-tricalcium phosphate composite available from Zimmer Inc., Warsaw, IN, cat. no. 97-1109-31). The hydroxyapatite or tricalcium phosphate may also be prepared by known methods, such as those disclosed by Termine et al, *Arch Biochem Biophys* (1970) 140:307–325, or by K. Hayashi et al, *Arch Orthop Trauma Surg* (1982, supra). In any event, the mineral is generally and preferably of non-biological origin and is supplied as a powder of appropriate mesh. Preferred particle sizes are in the range of 100–2000 um. While the mineral content of bone could be harvested and purified for this purpose, more economically prepared and controlled compositions are preferable, both as a matter of cost and of quality. If solid blocks are desired, these are prepared from the particulate form as described below.

The Collagen

The collagen component of the composition is critical to its efficiency. The collagen suitable for use in the invention is a purified atelopeptide fibrillar reconstituted collagen; it is typically prepared from skin.

Numerous forms of collagen have been prepared and they differ in their physical properties as well as in their biocompatibility. Where it is not intended to specify the particle size within the range of diameters over which a mixture will be a solution, colloid, or suspension, a single generic term, "collagen dispersion" is used. This term refers to any collagen preparation in aqueous medium where the collagen particle size is not specified, i.e., the preparation may be a solution, suspension, or gel.

Native collagen consists mainly of a triple helical structure containing repeating triplet sequences composed of glycine linked to two additional amino acids, commonly proline and hydroxyproline. Native collagen contains regions at each end which do not have the triplet glycine sequence, and thus do not form helices. These regions are thought to be responsible for the immunogenicity associated with most collagen preparations, and the immunogenicity can be mitigated by the removal of these regions to produce "atelopeptide" collagen. This can be accomplished by digestion with proteolytic enzymes, such as trypsin and pepsin. The nonhelical telopeptide regions are also responsible for natively occurring cross-linking, and atelopeptide collagen must be cross-linked artificially if cross-linking is desired.

Naturally occurring collagens have been subclassified into about ten types, depending on the amino acid sequence in the individual chains, the carbohydrate content, and the presence or absence of disulfide cross-links. The most common subtypes are Type I, which is present in skin, tendon, and bone, and which is made by fibroblasts; and Type III, which is found primarily in skin. Other types reside in specialized membranes or cartilage, or at cell surfaces. Types I and III contain similar numbers of amino acids in their helices and have a high degree of homology; however, Type III, but not Type I, contains two adjacent cysteines at the C-terminal ends of the triple helix, which are capable of forming inter-chain cross-links.

Therefore, collagen preparations may differ from each other by virtue of their initial compositions, which is a function of their origin, or by virtue of their modes of preparation. Collagen derived from bone, for example, contains exclusively Type I collagen; while collagen derived from skin also contains Type III. Also, the process of preparation may or may not remove the telopeptides. Thus both unaltered and "atelopeptide" collagen are possible. Cross-linking may be effected deliberately or accidentally. Sterilization by gamma-ray irradiation or by high heat may result in cross-linking without control of extent or nature and results in partial degradation of the triple helix; deliberate cross-linking may be carried out by a variety of means, including treatment with glutaraldehyde. Differences arising from perhaps more subtle causes are perhaps the result of variations in the details of the preparation procedure. For example, the collagen may be solubilized and re-precipitated, or may simply be finely divided and kept in suspension. When the solubilized material is reaggregated, the aggregation may be done in ways so as to form nonspecifically bonded solids, or the collagen may be reconstituted into fibers which simulate the native form. Also, of course, the degree of purity may vary.

As used herein, "free from impurities" or "purified" as regards collagen preparations refers to those impurities which are normally associated with collagen in its native state. Thus, collagen prepared from calfskin is free from impurities when other components of calfskin have been removed; that from bone when other components of bone are eliminated.

"Reconstituted" collagen refers to collagen which has been disassembled into individual triple helical molecules, with or without their telopeptide extensions, brought into solution and then regrouped into "fibrillar" forms. In this form, the fibrils consist of long, thin collagen molecules staggered relative to one another by multiples of about one-fourth their length. This results in a banded structure which can be further aggregated into fibers.

Collagen which is "substantially free from cross-linking" refers to collagen which has had the telopeptides removed, and thus lacks the native capacity for cross-link formation. These preparations remain substantially cross-link free if not deliberately cross-linked by, for example, being treated with glutaralde-hyde or subjected to treatment which itself results in cross-linking. For example, treatments often used for sterilizing purposes, such as high temperature and the gamma-radiation described herein when conducted under appropriate conditions, often result in cross-linking.

One collagen preparation which is suitable for the mixtures of the invention is an atelopeptide collagen which is reconstituted into fibrillar form and supplied as a dispersion of 5–100 mg/mL, preferably around 50–70 mg/mL. Such dispersions as Zyderm ® Collagen Implant (ZCI), which is commercially available in preparations containing 35 mg/mL collagen or 65 mg/mL collagen in saline, manufactured by Collagen Corporation, Palo Alto, Calif., are appropriate. For use in the compositions of the inventions, the ZCI or other collagen dispersions are used without lidocaine or other sedative drugs. As used herein, "ZCI" refers to the aqueous collagen dispersion, rather than to the collagen component per se.

The Collagen/Mineral Mixtures

The compositions of the invention which are eventually subjected to irradiation are generally initially prepared by mixing 50–85% by weight of calcium phosphate mineral component, preferably 65–75% mineral component, with the balance as a collagen dispersion in aqueous medium, such as ZCI. In terms of the mineral/collagen ratio (excluding the water content of the collagen dispersion), the mixtures are 60–98% mineral, preferably 75–98% mineral and the rest collagen. The composition may be prepared simply by thoroughly mixing the two components into a cohesive mass. The mixture can also be cast into a desired shape (e.g., blocks, squares, sheets). Cross-linking can be superimposed using, for example, glutaraldehyde to a level of 0.001–0.1% for either a dry or wet product, as further described below.

The mixtures are then dried to less than 1% moisture content and either rehydrated or heat treated before subjecting them to the sterilizing radiation procedures of the invention described below. The percentage compositions of the collagen/mineral and moisture content are calculated as follows: percentages of collagen and mineral are given as dry weights relative to the total weight of these two components alone, not including water. Percent moisture is the weight water divided by the total weight (water +collagen +mineral) times 100.

The sterilized material resulting from the radiation process may be used as mineral/collagen per se or may be mixed with additional components, which are also sterilized, as appropriate, for administration to the subject. The water content is preferably in the range of about 2–10%. The preparations, while being described in terms of collagen and mineral, are usually applied to the subject in a wetted condition and contain either the inherent moisture of the original mixture or are rewetted with sterile water or saline before administration. Alternatively, one may apply the preparation in dry form, and rely on moisture present at the administration site. In addition, components designed to increase the efficacy of the compound may be added, such as blood or bone marrow. As stated above, the percentages of collagen and mineral reflect their relative amounts, and the collagen/mineral mixture can form as little as 10% of the total preparation applied in some instances. Any additives must themselves also be sterilized, or be derived from such source that sterilization is irrelevant, as is the case for blood, for example.

Desired Properties of the Mixture

The collagen/mineral mixture itself, depending on its application, needs to exhibit certain physical properties. Specifically, it needs to be resilient enough to permit some shaping, but at the same time must be sufficiently rigid to resist total disorganization when stressed. Resistance to compression can be measured as the compressive modulus, using commercially available equipment, such as Instron Universal Testing Instrument Model 4202, and according to guidelines for measurement of compressive modulus as published by the American Society for Testing Materials (ASTM).

To conduct this measurement, the mixtures are first soaked for 5-24 hours in physiological saline. This gives more relevant data, as the material will be wet when implanted. The soaking is done for a sufficient time to insure complete wetting; the mixture is then placed in the test apparatus. If the material is resilient, it will compress easily until a point is reached wherein, in order further to compress the material, it is necessary to disrupt the inherent structure at the microscopic level. If the material is rigid, this point will be reached with less deformation than for resilient material. For collagen/mineral mixtures, the microscopic organization is maintained first by the triple helix per se, but also by interaction between the collagen triple helical portions of the individual components of the fibrils as well as binding of the fibrils to each other. Compression disrupting any of these levels of organization will be more difficult than general compression which decreases the volume of empty space. Of course, the more highly organized and cross-linked the collagen chains in the composition, the more difficult this microscopic compression is.

Thus, a high compressive modulus (measured in $N/cm^2$) indicates a high level of organization at the microscopic level, specifically, a high level of cross-linking. A low compressive modulus indicates that cross-linking is low. For appropriate physical handling properties and for maintenance of integrity as an implant, it is important that the compressive modulus be reasonably high, at least about 10 $N/cm^2$ or more, and may be as high as 35-45 $N/cm^2$. The upper levels of compressive modulus are imposed by the nature of the materials, and it is believed that mixtures of this type cannot, in fact, attain modulus values of much greater than 100 $N/cm^2$ under any degree of cross-linking. In any event, it is significant in maintaining suitable physical properties for the compositions of the invention that the compressive modulus be above 10 $N/cm^2$, and a preferred range is 10-60 $N/cm^2$, most preferably 25-45 $N/cm^2$. The resultant composition after the treatment according to the process of the present invention is assessed by this measure in order to verify that the appropriate compressive resistance strength is attained.

The strength of rigid compositions of the invention is measured in terms of tensile strength. Tensile strength is determined by the amount of force necessary to separate two ends of a rigid implant form (rupture force) divided by the cross-sectional area of the form, using a standard protocol for determining tensile strength. The rigid compositions of the invention exhibit a tensile strength of at least about 1 $N/cm^2$, preferably about 3-12 $N/cm^2$.

While the mixture needs to maintain integrity at a microscopic level, it must also be sufficiently porous and vulnerable to have biological properties which permit ingrowth of surrounding hard tissue, and in some cases should exhibit resorbability when placed in a subject. However, this is a property that needs to be optimized rather than maximized. It is reflected as a modest degree of degradation of the collagen fibrils, which makes them susceptible to biological processes when placed in the subject.

One in vitro measurement of this characteristic is susceptibility to hydrolysis by trypsin or "trypsin sensitivity". To effect this measurement, the samples are treated with the protease trypsin, which is capable of attacking only fragmented portions of the collagen protein. The extent of hydrolysis is measured by fluorescamine assay for solubilized peptides, and the results are expressed as percentage nonhelical collagen. For example, and for comparison, gelatin preparations of collagen are 100% nonhelical, collagen in solution is about 10% nonhelical, and ZCI is 10% nonhelical. Desirable ranges depend on the use intended.

An alternative measure of fragmentation at a microscopic level is the transition temperature as measured by differential scanning calorimetry (DSC). A lowering of the transition temperature indicates an increase in fragmentation at a microscopic level in a manner similar to that measured by trypsin sensitivity.

The process of the invention permits adjustment of the foregoing parameters to achieve optimum physical and biological compatibility properties. The process also results in efficient sterilization of the material, assuring sterilization levels at least as low as $10^{-6}$.

Method of the Invention

Sterilization and optimization of physical properties are achieved by subjecting the compositions to irradiation using a gamma radiation source in the range of 0.5-4 Mrad, preferably 1-3 Mrad, and most preferably 2.5-3 Mrad. These dosages are known to effect sterilization of preparations containing only collagen (see Artandi, (supra)). The irradiation process itself is carried out using standard procedures known per se in the art for sterilization of foodstuffs, cosmetics, and the like. The irradiation is conducted using a gamma-emitting source, such as $^{131}I$, $^{137}Cs$, or, most commonly, $^{60}Co$. These materials are supplied in standard forms and applied to samples using standard equipment by AEC licensees according to established guidelines. Reference is made to *Process Control Guidelines for Gamma Radiation Sterilization of Medical Devices* published by Assn. for Advancement of Medical Instrumentation (1984) as AAMI Recommended Practice. Reference is made also to Technical Reports Series 149; "Manual on Radiation Sterilization of Medical & Biological Materials", Intl Atomic Energy Commission, Vienna 1973.

The significant factors in the effect of the radiation on the sample are the total dosage (Mrad) and the state of the sample while being irradiated. Other factors, such as the rate at which the energy is supplied, total radiation time, distance of the sample from the source, and so forth, are generally irrelevant except as to their combined effect on total dosage.

The condition of the sample subjected to the radiation is of the utmost importance, and forms the basis for the invention herein. The sample must either be provided with a desired level of cross-linking before being subjected to the radiation, or must be placed in a condition during the radiation so as to permit the radiation itself to effect this cross-linking, or a combination of these factors must be used.

In one preferred method of carrying out the invention, the mixture is assured to contain a moisture content of 1-6%, preferably 1-2%, during the application of the gamma-radiation. This is most conveniently achieved by first drying the mixture to a moisture content of less than 1% by dry heat at 35-45° C., preferably 35-37° C., and then rehydrating the mixture by treating it for 6-24 hours at 35-45° C. at 50-95% relative humidity (RH), preferably 35-37° C. at 50-80% RH, to achieve the desired equilibrium moisture content. The moisture content can be measured by standard techniques such as that described by K. Fischer, *Angew Chem* (1935) 48:394 to assure that the desired range is achieved. Other protocols to achieve the desired level of moisture can also be used, and the water content verified as described. When the mixture has the desired level of moisture, it is subjected to the radiation dosage described. Crosslinking linking to the desired level then occurs during the irradiation.

In an alternative embodiment, cross-linking is induced by heating prior to irradiation. In one preferred protocol, the sample is first dried, to a moisture content of less than 1%, or preferably 0.5-1% as above, and then heated for 4-24 hours at about 60-90° C., preferably 70-80° C. at 20-80% relative humidity, preferably 50-60% relative humidity to effect a desired level of cross-linking, as measured by the compressive modulus. Suitable values for the compressive modulus are 10-45 N/cm$^2$. Alternative means to achieve this level of cross-linking are also available, including treatment with cross-linking agents, such as glutaraldehyde or formaldehyde. In any case, the sample is subjected to these cross-linking treatments until a suitable measure of cross-linking by compressive modulus is attained. The sample is then subjected to the radiation.

Thus, in the first embodiment above, crosslinking is believed to occur during the radiation process due to the presence of moisture in the sample; in the second approach, the cross-linking is effected prior to the radiation treatment and is not greatly increased during sterilization. However, it is clear that a combination of the two foregoing treatments can be employed by reducing the degree of cross-linking in the preradiation treatment and adjusting the moisture content of the sample during radiation so as to complete the desired process. The general aspects of the foregoing preferred procedures are set forth in FIG. 1.

For the irradiation step, the compositions, suitably prepared for radiation treatment as above, are packaged in materials compatible with gamma radiation to preserve the sterilization of the samples contained, and are then subjected to 0.5-4 Mrad of radiation, according to standard procedures. The samples as then packaged are in a form suitable for reconstitution under sterile conditions and application to the subject. For such use, the sample is removed from the package under sterile conditions and soaked in sterile saline or mixed with blood or bone marrow, as desired, and used for its desired purpose.

Another presently-preferred embodiment of the invention is prepared by mixing fibrillar collagen (Zyderm ® II, 65 mg/mL collagen dispersion) with hydroxyapatite having a mesh size of 20-40, at a ratio of 35% collagen:65% HA. The mixture is then placed in molds or trays, and is dried at 37° C. for 48 hours at a relative humidity of <10%, providing a product having 28.6:1 HA:collagen. The dry product is then rehumidified at 47° C., 90% RH for 8 hours, and is then irradiated at 2.5-3.0 Mrads. The final product contains 3-5% collagen, 91-95% hydroxyapatite, and 2-4% moisture.

Another presently preferred embodiment is prepared by mixing 65 mg/mL fibrillar collagen (Zyderm ® II) and a mixture of hydroxyapatite and tricalcium phosphate (60:40) as 0.5-1.0 mm size granules. These components are mixed at a ratio of 65% fibrillar collagen, 35% HA/TCP, and the mixture poured into molds or trays. The mixture is dried at 37° C. for 48 hours at a relative humidity of <10%, providing a product having 8.3:1 HA/TCP:collagen. The dry product is then rehumidified at 47° C., 90% RH for 8 hours, and is then irradiated at 2.5-3.0 Mrads. The resulting product contains about 10-13% collagen, about 82-89% HA/TCP, and about 2-5% moisture.

Another presently preferred embodiment of the invention is prepared by mixing fibrillar collagen (25 mg/mL collagen dispersion) with hydroxyapatite/tricalcium phosphate (60:40) as 0.5-1.0 mm granules, at a ratio of 72.7% collagen:27.3% HA/TCP. The mixture is poured into trays or molds and is lyophilized, first cooling down to 3° C. over 30 minutes, holding at 3° C. for 60 minutes, cooling down to −20° C. over 45 minutes, holding at −20° C. for 120-240 minutes, and evacuating the chamber and raising to 20° C. over 60 minutes, and holding at 20° C. for 960 minutes. The product is then rehumidified at 20° C. and 95% RH for 6 hours, and is irradiated at 2.3-2.7 Mrads, to provide a product having a final composition of about 6-12% collagen, 78-89% HA/TCP, and 5-15% moisture.

If desired, the compositions of the invention may additionally incorporate an antibiotic or combination of antibiotics (e.g., penicillin, streptomycin, tetracycline, sulfamethoxazole, and the like, preferably tetracycline) in order to prevent postoperative infection, or to treat existing infection in the bone and tissue surrounding the implantation site. The antibiotic may be incorporated at any point during or after the implant manufacture, and is preferably incorporated by soaking the implant in an antibiotic solution. When present, the implant will generally contain an effective amount of antibiotic. The effective amount will vary with the age and condition of the subject to be treated, the nature and severity of the condition, and the efficacy of the antibiotic selected. The effective amount can be determined by one of ordinary skill in the art. However, in general terms, an effective amount will be in the range of 5-3,000 mg/implant for sulfamethoxazole and other sulfa drugs, 0.5-3,000 mg/implant for streptomycin and other aminoglycosides, 5-2,000 mg/implant for cefaclor and other cephalosporins, 0.5-3,000 mg/implant for tetracycline, erythromycin and related macrolide antibiotics, 0.5-3,000 mg/implant for penicillin, ampicillin, amoxycillin, and related derivatives.

Use of the Composition

The resulting composition is used to augment bone and fill bony defects, for example, bone nonunions, fresh fractures, periodontal bony pockets, tooth extraction sockets, and jaw cysts. An important example of inlay procedures includes alveolar ridge augmentation. The procedures for the surgical implantation are known in the art. For alveolar ridge augmentation, the composition is inserted under the periosteum in places where augmentation is desired. In orthopedic and reconstructive applications, mineral in the form of porous blocks may also be indicated, particularly where the graft must bear stress. Implantation of the collagen-impregnated blocks is also effected by standard surgical techniques.

Some medical indications are preferably treated with resorbable graft materials, while others are best treated with nondegradable materials. For example, nondegradable implants are indicated for reconstructive or bone augmentation procedures such as alveolar ridge or chin augmentation, or mandibular advancement. Resorbable materials are preferred for filling in spaces to be replaced by normal bone, such as gaps caused by trauma or disease.

Turnover of collagen is controlled by the extent of crosslinking, which may be naturally occurring or introduced through chemical or physical treatment. Degradation of calcium phosphate can be controlled by varying the porosity, surface area, apatite or betawhitlockite crystallographic structure, or inclusion of ions such as fluoride, carbonate, or magnesium.

EXAMPLES

The following examples are meant to illustrate the invention, but not intended to limit its scope.

EXAMPLE 1

Preparation of Basic Compositions (A) A mineral/collagen preparation was obtained by mixing 65 parts by weight of OrthoMatrix ™ HA-1000 ™ hydroxyapatite with 35 parts by weight of Zyderm® II Collagen Implant (65 mg/mL) without lidocaine. Since ZCI is a 6.5% collagen-in-saline preparation, the final composition is 65 parts HA, 2.3 parts collagen ($0.065 \times 35$) and 32.7 parts ($35 \times 2.3$) saline, all by weight.

The mixture was thoroughly mixed, and portions measuring 0.55 mL were extruded into blocks and dried under a laminar flow hood for about 48 hr at 36-37° C. The resulting preparation had a moisture content of 0.87%, as measured by the method of K. Fischer, *Angew Chem* (1935) 48:394. The composition is thus 0.87% water, 3.37% collagen, and 95.76% mineral, all by weight as defined above.

(B) Another composition of the invention was prepared by mixing fibrillar collagen (Zyderm® II, 65 mg/mL) with hydroxyapatite having a mesh size of 20-40, at a ratio of 35% collagen:65% HA. The mixture was then placed in trays, and was dried at 37° C. for 48 hours at a relative humidity of <10%, providing a product having 28.6:1 HA:collagen. The dry product was then rehumidified at 47° C., 90% RH for 16 hours, and was irradiated at 2.5-3.0 Mrads. The final product contained 3.4% collagen, 94.6% hydroxyapatite, and about 2% moisture.

Analysis by differential scanning calorimetry (DSC) revealed a melting transition at about 53.7° C. (14.8 cal/g). The product exhibited a compression strength of about 34.9 N/cm$^2$, and a trypsin sensitivity of about 11%.

(C) Another composition of the invention was prepared by mixing fibrillar collagen (Zyderm® II) and a mixture of hydroxyapatite and tricalcium phosphate (60:40) as 0.5-1.0 mm size granules. These components were mixed at a ratio of 65% fibrillar collagen, 35% HA/TCP, and the mixture poured into trays ($3 \times 1 \times 0.33$ mm). The mixture was dried at 37° C. for 48 hours at a relative humidity of <10%, providing a product having 8.3:1 HA/TCP:collagen. The dry product was then rehumidified at 47° C., 90% RH for 6-8 hours, and was irradiated at 2.3-2.7 Mrads. The resulting product contained about 10.8% collagen, about 87.2% HA/TCP, and about 2% moisture.

Analysis by differential scanning calorimetry (DSC) revealed a melting transition at about 56° C. (63.1 cal/g). The product exhibited a tensile strength of 6-9.5 N/cm$^2$, and a trypsin sensitivity of about 0.7-8.3%.

(D) Another composition of the invention was prepared by mixing fibrillar collagen (25 mg/mL) with hydroxyapatite/tricalcium phosphate (60:40) as 0.5-1.0 mm granules, at a ratio of 72.7% collagen/27.3% HA. The mixture was poured into trays ($3 \times 1 \times 0.33$ mm) and lyophilized, first cooling down to 3° C. over 30 minutes, holding at 3° C. for 60 minutes, cooling down to $-20°$ C. over 45 minutes, holding at $-20°$ C. for 120-240 minutes, and evacuating the chamber and raising to 20° C. over 60 minutes, and holding at 20° C. for 960 minutes. The product was then rehumidified at 20° C. and 95% RH for 6 hours, and was irradiated at 2.3-2.7 Mrads, to provide a product having a final composition of about 6% collagen, about 84% HA/TCP, and about 10% moisture.

Analysis by differential scanning calorimetry (DSC) revealed a melting transition at 49.7±1.1° C. (32.75±9.8 cal/g). The product exhibited a tensile strength of 3.56±2.25 N/cm$^2$, and a trypsin sensitivity of about 13.7%. (Data are reported as mean ± standard deviation for two trials.)

EXAMPLE 2

Effect of Moisture Content

The blocks prepared to according to Example 1(A) were set into vials for rehumidification. Twenty vials were incubated at 75% relative humidity, 35° C. for about 24 hr to obtain blocks with a moisture content measuring 1.86%. Ten of these were further subjected to 95% relative humidity at 36-43° C. for 15-½ hr to obtain a moisture content of 5.9%.

Figure 2A:
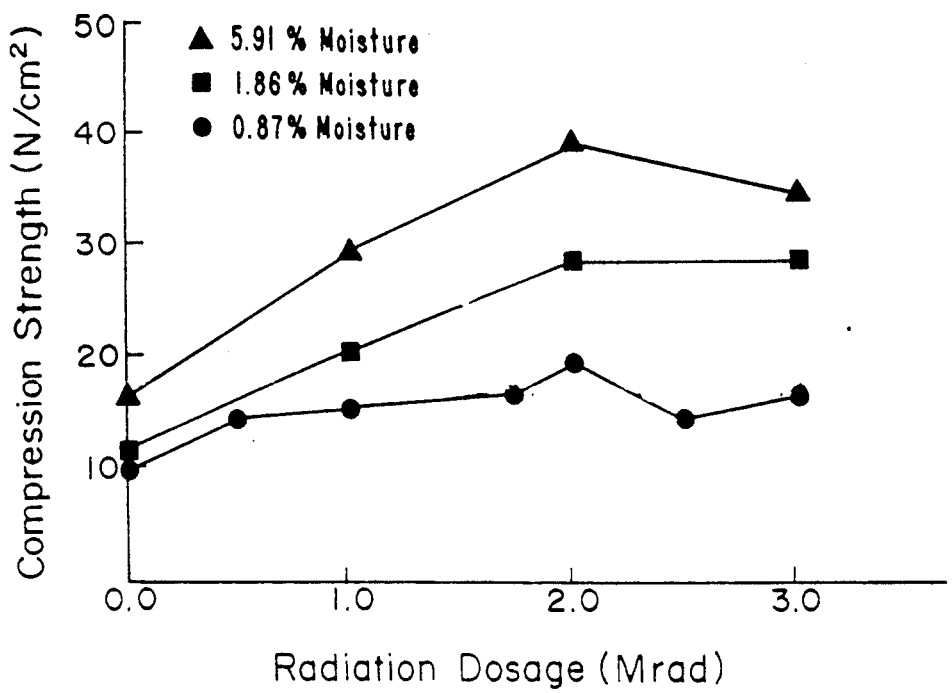
FIG. 2a shows the effect of moisture content of collagen/mineral mixtures on compressible modulus at various levels of irradiation.
Figure 2B:
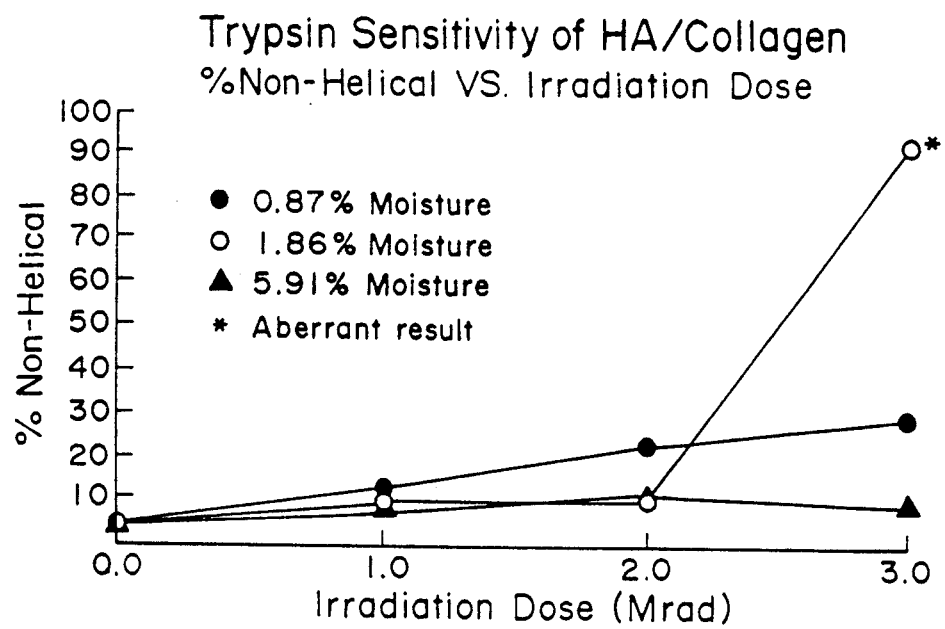
FIG. 2b shows this effect on trypsin sensitivity.

The dry and rehumidified samples were subjected to varying levels of total radiation ranging from 0.5 to 3 Mrad. The results of the radiation on the compression modulus are shown in FIG. 2a, and the effect on trypsin sensitivity is shown in FIG. 2b. These results show that samples containing 1.86% moisture content were strengthened by the radiation procedure in terms of compression modulus, while their trypsin sensitivity was not markedly increased. In contrast, samples not rehumidified showed considerable fragmentation during irradiation, and the compressive strength was not measurably improved. (All samples showed a modest decrease in the transition temperature when measured by DSC.)

Figure 3A:
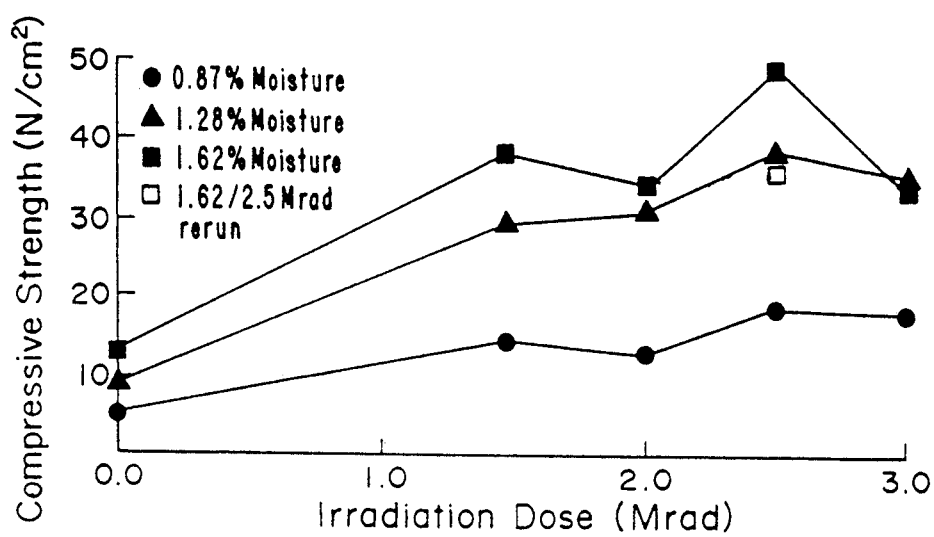
FIGS. 3a and 3b show the results of independent determinations similar to those of FIGS. 2a and 2b.
Figure 3B:
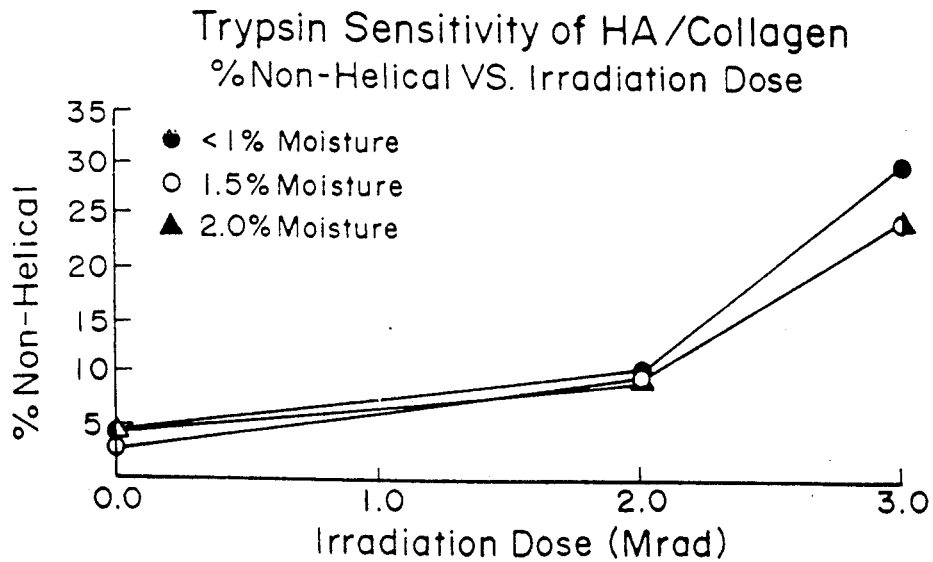

The foregoing procedure was repeated, this time rehumidifying the samples to 1.28% and 1.62% moisture content, and gave comparable results, as shown in FIGS. 3a and 3b, respectively. Again, the samples containing a higher moisture content exhibited less fragmentation during irradiation, according to the trypsin sensitivity assay (FIG. 3b), but markedly increased in compression modulus during radiation, as shown in FIG. 3a.

EXAMPLE 3

Effect of Pretreatment with Heat

The samples prepared as in Example 1(A) were placed in vials and 16 vials stoppered and treated at 80° C. at 50-70% RH for 48 hrs. The effects of radiation on these heat-treated samples was compared to samples not heat treated, but containing the original 0.87% moisture content. The trypsin sensitivity of the heat-treated samples increased from a value showing 10% non-helical collagen for nonirradiated samples to 60% non-helical content for samples irradiated with 3 Mrad, in contrast to a relatively low fragmentation increase of 3% non-helical character to about 25% at 3 Mrad for the samples not heat-treated. The compressive strength of the sample was measurably increased by the heat treatment, measuring about 35 N/cm² before radiation and maintaining this level throughout the dosage range.

In a separate experiment, samples containing 0.87% moisture heated for only 6-½hrs at 80° C. and 50-70% RH also showed a compressive modulus of 35 N/cm².

Thus, it appears that heat-treated materials maintain their capacity to resist compression after radiation, while having increased trypsin sensitivity.

EXAMPLE 4

Effect of Heat Curing Alone

Samples were prepared as in Example 1(A), except that the extruded mixture was incubated for 72 hr at 26-34° C. at 90-95% relative humidity before drying, as described above, to obtain a moisture content of 0.48-0.49%. When this preincubated mixture was treated for varying lengths of time at 80° C. at 50-70% RH it showed a consistent increase in compressive modulus, from 15 N/cm² with no heat treatment, to 25 N/cm² after 4 hours at 80° C., 30 N/cm² after 8 hours, and 40 N/cm² after 12 hours. Therefore, heat treatment is effective in increasing the compressibility of dried samples as is the application of radiation; however, sterilization does not necessarily result.

I claim:

1. A biocompatible collagen/mineral composition which comprises a mixture containing 2-40% reconstituted fibrillar atelopeptide collagen and 60-98% calcium phosphate mineral by weight exclusive of moisture, which composition has a sterility assurance factor of at least as low as $10^{-6}$ and an additional characteristic selected from the group consisting of a compressive modulus of at least 10 N/cm² and a tensile strength of about 3-12 N/cm².

2. The composition of claim 1 which has a moisture content of 0.5-15 wt%.

3. The composition of claim 1 which has a collagen content of about 10-13%, and a calcium phosphate mineral content of about 82-90%.

4. The composition of claim 1 which has a collagen content of about 6-12%, and a calcium phosphate mineral content of about 78-89%.

5. The composition of claim 1 which further comprises an antibiotic.

6. A biocompatible collagen/mineral composition which comprises a mixture containing 2-40% reconstituted fibrillar atelopeptide collagen and 60-98% calcium phosphate mineral by weight exclusive of moisture, which composition has a sterility assurance factor of at least as low as $10^{-6}$ and an additional characteristic selected from the gruop consisting of a compressible modulus in the range of 25-45 N/cm² and a tensile strength of about 3-12 N/cm².

* * * * *